United States Patent [19]

Fuyama et al.

[11] 4,283,415

[45] Aug. 11, 1981

[54] OIL-IN-WATER INSECTICIDAL AND ACARICIDAL EMULSION

[75] Inventors: Hiroshi Fuyama, Ikeda; Kozo Tsuji, Takatsuki, both of Japan

[73] Assignee: Sumitomo Chemical Company Limited, Osaka, Japan

[21] Appl. No.: 50,286

[22] Filed: Jun. 20, 1979

[30] Foreign Application Priority Data

Jul. 7, 1978 [JP] Japan .................................. 53-83200

[51] Int. Cl.³ ............................................. A01N 37/34
[52] U.S. Cl. .................................... 424/304; 424/168; 424/305; 424/306
[58] Field of Search ................. 424/304, 305, 306, 168

[56] References Cited

U.S. PATENT DOCUMENTS

| 3,835,176 | 9/1974 | Matsuo et al. | 260/465 D |
|---|---|---|---|
| 3,973,035 | 8/1976 | Searle et al. | 424/304 |
| 3,973,036 | 8/1976 | Hirano et al. | 426/304 |
| 4,071,617 | 1/1978 | Graves et al. | 424/78 |

Primary Examiner—Leonard Schenkman
Attorney, Agent, or Firm—Sughrue, Mion, Zinn, Macpeak and Seas

[57] ABSTRACT

An oil-in-water insecticidal and acaricidal emulsion comprising 1 to 50% by weight of as a hydrophobic insecticidally and acaricidally active liquid ingredient at least one ester of the formula (I):

where X is a hydrogen atom, a chlorine atom, a bromine atom or a fluorine atom; and Y is a group of the formula:

where $R_1$ is a methyl group or a group of the formula:

where $R_5$ is a chlorine atom, a bromine atom, a fluorine atom or a methyl group; $R_2$ is a hydrogen atom or a methyl group; $R_3$ is a chlorine atom, a bromine atom, a fluorine atom or a tert-butyl group; and $R_4$ is an isopropyl group or a cyclopropyl group; 2 to 10% by weight of polyvinyl alcohol or gum arabic; and 0.1 to 20% by weight of a thickener with the balance being water.

12 Claims, No Drawings

OIL-IN-WATER INSECTICIDAL AND ACARICIDAL EMULSION

BACKGROUND OF THE INVENTION

1. Field of the Invention

This invention relates to a novel oil-in-water insecticidal and acaricidal emulsion (generally called an "aqueous flowable formulation"), which comprises as a hydrophobic insecticidally and acaricidally active liquid ingredient 1 to 50% by weight of at least one ester of the formula (I):

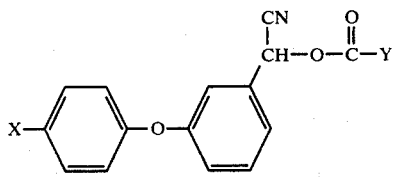

where X is a hydrogen atom, a chlorine atom, a bromine atom or a fluorine atom; and Y is a group of the formula:

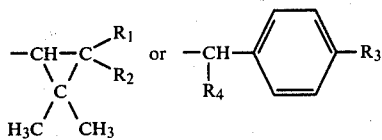

where $R_1$ is a methyl group or a group of the formula:

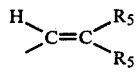

where $R_5$ is a chlorine atom, a bromine atom, a fluorine atom or a methyl group; $R_2$ is a hydrogen atom or a methyl group; $R_3$ is a chlorine atom, a bromine atom, a fluorine atom or a tert-butyl group; and $R_4$ is an isopropyl group or a cyclopropyl group, 2 to 10% by weight of polyvinyl alcohol or gum arabic; and 0.1 to 20% by weight of a thickener with the balance being water. The insecticidal and acaricidal emulsion of the invention exhibits an insecticidal and acaricidal activity equivalent to a conventional formulation and at the same time it is stable and easier to use.

2. Description of the Prior Art

Of conventionally employed pesticidal formulations in a liquid form, an emulsifiable concentrate which generally consists of a pesticidally active ingredient, a synthetic surfactant and a large amount of an organic solvent often has defects derived from the organic solvent contained therein, such as flammability or malodor, toxicity or irritation to humans, cattle or other domestic animals or poultry, phytotoxicity against crops, and the like.

A wettable powder which does not use an organic solvent is also not fully satisfactory because a spray liquid cannot readily be prepared due to dustiness of its fine powder and aerial low volume application in high concentration (less than 300 ml per 10 ares) is impossible.

For these reasons, studies have been made on aqueous flowable formulations of pesticides and transparent emulsions which replace the organic solvent or powder carrier with water to suspend or disperse fine particles of a hydrophobic pesticidally active ingredient.

Since such aqueous flowable formulations and transparent emulsions are handled in a liquid form, a spray liquid can be prepared without producing dust; and measuring the volume, dilution and other necessary operations can be achieved as easily as with conventional liquid type formulations. In addition, it is accompanied by few or none of the problems of an organic solvent which is toxic or irritating to humans, cattle or other domestic animals or poultry, as well as causes phytotoxicity against crops. However, most aqueous flowable formulations of pesticides hitherto proposed are suspensions using a solid hydrophobic pesticidally active ingredient (such as those disclosed in Japanese Patent Application (OPI) Nos. 126635/74, 76236/75 and 148625/77 (the term "OPI" as used herein refers to a "published unexamined Japanese patent application"); and U.S. Pat. No. 4,071,617), and no practical oil-in-water emulsion that uses a pesticidally active ingredient in an oil form has yet been developed due to difficulties in stabilizing its physical properties over an extended period of time.

Transparent emulsions used as oil-in-water pesticidal compositions are disclosed in Japanese Patent Publication No. 20520/71, and Japanese Patent Application (OPI) Nos. 54547/74 and 122628/77, but these transparent emulsions are a water soluble type that uses a large quantity of a general-purpose synthetic surfactant to reduce the particle size of the pesticidally active ingredient to less than $0.1\mu$, and no satisfactory technique has been proposed to solve the cost and toxicity problems which accompany the use of large quantities of surfactant.

SUMMARY OF THE INVENTION

Various studies have been directed to a method of producing an oil-in-water insecticidal and acaricidal emulsion which contains a compound of the formula (I) as a hydrophobic active liquid ingredient and which retains its chemical and physical properties for an extended period of time and is able to exhibit an insecticidal and acaricidal effect comparable to the above described conventional formulations but which, unlike the conventional formulations, does not employ an organic solvent or a general-purpose synthetic surfactant such as a higher alcohol sulfate, a higher alcohol sulfonate, an alkyl sulfonate, an aryl sulfonate, an alkyl aryl sulfonate or a formalin condensate thereof, a fatty acid ester compound, a polyoxyethylene alkyl ether, a polyoxyethylene aryl ether, a polyoxyethylene alkyl aryl ether, a polyoxyethylene phenyl phenol derivative or a polyoxyethylene sorbitan alkylate and the like. As a result of these studies, the present inventors have found that polyvinyl alcohol or gum arabic is the most suitable dispersing agent for compounds of the formula (I).

Accordingly, it is a principal object of the present invention to provide an insecticidally and acaricidally active oil-in-water emulsion which retains its physical and chemical properties for an extended period of time.

More particularly, it is an object of the present invention to provide an insecticidally and acaricidally active oil-in-water emulsion which is free from the drawbacks which accompany the conventional use of general-purpose synthetic surfactants and organic solvents.

It is another object of the present invention to provide an insecticidally and acaricidally active oil-in-water emulsion based on compounds of the formula (I).

DETAILED DESCRIPTION OF THE INVENTION

An insecticidal and acaricidal emulsion that meets the requirements described above can be economically prepared by a simple method which comprises dispersing by mechanical means fine particles (or fine droplets) of a compound of the formula (I) in an aqueous solution of polyvinyl alcohol or gum arabic and adding a suitable thickener to stabilize the suspended fine particles of the compound.

A brief description of the method of producing the oil-in-water insecticidal and acaricidal emulsion of this invention will be given below. First, a hydrophobic insecticidally and acaricidally active liquid ingredient of the formula (I) is added to a 2 to 20 wt% aqueous solution of polyvinyl alcohol or gum arabic, and a conventional stirrer such as a T.K. Homomixer (a homogenizer manufactured by Tokushu Kika Koguo Co., Ltd.) or a Shinagawa All-Purpose Mixer (a mixer manufactured by San-Ei Seisakusho, Ltd.) is used to disperse the particles of the active ingredient (A.I.) while the aqueous solution is heated at 60° to 70° C. The size of the emulsified particles of the active ingredient can be varied within the range of from about 1 to 200$\mu$ depending upon the stirring force or the content of polyvinyl alcohol or gum arabic. A microscope is used to check the size of the emulsified particles of the active ingredient. Finally, for the purpose of preventing settling of the emulsified particles and improving the dispersion stability, an aqueous solution of a thickener is added to the emulsion in a suitable amount. The resulting oil-in-water insecticidal and acaricidal emulsion remains stable for an extended period.

While typical examples of the compound of the formula (I) according to this invention are hereunder given, it is to be understood that they are by no means meant to limit the scope of this invention and that optical isomers and/or geometric isomers of those examples are included within the scope of the compound. It is also to be understood that the compound is liquid at room temperature (e.g., about 20° C.). Representative examples include: $\alpha$-cyano-3-phenoxybenzyl 2-(4-chlorophenyl)isovalerate, $\alpha$-cyano-3-phenoxybenzyl (+)-2-(4-chlorophenyl)isovalerate, a mixture comprising more than 60% of (−)-$\alpha$-cyano-3-phenoxybenzyl (+)-2-(4-chlorophenyl)isovalerate and (+)-$\alpha$-cyano-3-phenoxybenzyl (−)-2-(4-chlorophenyl)isovalerate, $\alpha$-cyano-3-(4-bromophenoxy)benzyl 2-(4-chlorophenyl)isovalerate, $\alpha$-cyano-3-phenoxybenzyl 2(4-tert-butylphenyl)isovalerate, $\alpha$-cyano-3-(4-fluorophenoxy)benzyl 2-(4-chlorophenyl)isovalerate, $\alpha$-cyano-3-(4-bromophenoxy)benzyl 2,2-dimethyl-3-(2,2-dichlorovinyl)cyclopropanecarboxylate, $\alpha$-cyano-3-(4-fluorophenoxy)benzyl 2,2-dimethyl-3-(2,2-dichlorovinyl)cyclopropanecarboxylate, $\alpha$-cyano-3-phenoxybenzyl chrysanthemate, $\alpha$-cyano-3-pehnoxybenzyl 2,2-dimethyl-3-(2,2-dichlorovinyl)cyclopropanecarboxylate, and $\alpha$-cyano-3-phenoxybenzyl 2,2,3,3,-tetramethylcyclopropanecarboxylate.

The oil-in-water insecticidal and acaricidal emulsion in accordance with the present invention comprises 1 to 50% by weight, preferably 1 to 40% by weight of as a hydrophobic insecticidally and acaricidally active liquid ingredient at least one ester of the formula (I); 2 to 10% by weight of polyvinyl alcohol or gum arabic; and 0.1 to 20% by weight, preferably 0.4 to 10% by weight of a thickener with the balance being water.

A suitable example of the polyvinyl alcohol that can be used in this invention has a degree of polymerization less than about 1500 and a degree of hydrolysis between about 70 to 90 mol%. One such example is Gohsenol GL-05 (polyvinyl alcohol manufactured by The Nippon Synthetic Chemical Industry Co., Ltd. having a degree of polymerization of less than 1,000 and a degree of hydrolysis of from 86.5 to 89 mol%).

Examples of the thickener that can be used in this invention include tragacanth gum, guar gum, sodium alginate, sodium carboxymethylcellulose, sodium carboxymethyl starch, hydroxyethylcellulose, methylcellulose, polyacrylic acid or derivatives thereof, etc. Commercially available thickeners include Agrisol FL-100F (a product of Kao-Atlas Co., Ltd.), Primal ASE-60 (a product of Japan Acrylic Chemical Co., Ltd.), Rheogic 250H (a product of Nihon Junyaku Co., Ltd.) and Carbopol (a product of The B.F. Goodrich Company). These thickeners are used in an amount within the range of from 0.1 to 20 wt%, and the optimum amount of addition varies from thickener to thickener and preferably ranges from 0.4 to 10 wt%.

Since the oil-in-water insecticidal and acaricidal emulsion of this invention contains no organic solvent, it is free from potential hazards such as flammability and malodor of an organic solvent and its toxicity or irritation to humans, cattle or other domestic animals or poultry, or phytotoxicity against crops. In addition, because of high miscibility with water used as a diluent for preparation of a spray liquid, measuring the volume, dilution and other necessary operations can be performed with ease which is comparable to the case of the conventional liquid type formulations.

This invention will hereunder be described in greater detail by reference to the following Examples which are given here for illustrative purposes only and are by no means intended to limit the scope of this invention.

EXAMPLE 1

10 g of (±)-$\alpha$-cyano-3-phenoxybenzyl (±)-2-(4-chlorophenyl)isovalerate was added to 40 g of a 10 wt% aqueous solution of Gohsenol GL-05, and the mixture was stirred at 70° C. with a T.K. Homomixer at 5000 rpm for a period of 5 minutes.

To the mixture was added 50 g of a neutralized 20 wt% aqueous solution of Agrisol FL-100F at ambient temperature, and the resultant mixture was lightly stirred for a few minutes to obtain 100 g of a homogeneous oil-in-water insecticidal and acaricidal emulsion containing 10 wt% of (±)-$\alpha$-cyano-3-phenoxybenzyl (±)-2-(4-chlorophenyl)isovalerate. The particles of the emulsified active ingredient were in the range of from 1 to 60$\mu$ in size.

As is clear from Table 1 below which indicates the results of test for dispersion stability, the insecticidal and acaricidal emulsion of this invention was stable in its chemical and physical properties.

TABLE 1

| Storage Conditions | Stability Test for the Insecticidal and Acaricidal Emulsion of Example 1 | |
|---|---|---|
| | Percent Decomposition of A.I.* | Dispersion Stability |
| 40° C. | | |

TABLE 1-continued

Stability Test for the Insecticidal and Acaricidal Emulsion of Example 1

| Storage Conditions | Percent Decomposition of A.I.* | Dispersion Stability |
| --- | --- | --- |
| 1 month | 0 | uniform dispersion without settlement of A.I. |
| 3 months | 0.2 | uniform dispersion without settlement of A.I. |
| 6 months | 0.5 | uniform dispersion without settlement of A.I. |
| 50° C. | | |
| 1 month | 0 | uniform dispersion without settlement of A.I. |
| 3 months | 1.3 | uniform dispersion without settlement of A. I. |
| 6 months | 3.0 | uniform dispersion without settlement of A.I. |

*based on the A.I. content determined at the time of preparation

EXAMPLE 2

The procedure of Example 1 was repeated except that the T.K. Homomixer was rotated at 2500 rpm. The product was 100 g of an oil-in-water insecticidal and acaricidal emulsion containing 10 wt% of (±)-α-cyano-3-phenoxybenzyl (±)-2-(4-chlorophenyl)isovalerate. The particles of the emulsified active ingredient were in the range of from 5 to 160μ in size.

As is clear from Table 2 below which indicates the results of test for dispersion stability, the insecticidal and acaricidal emulsion of this invention was stable in its chemical and physical properties.

TABLE 2

Stability Test for the Insecticidal and Acaricidal Emulsion of Example 2

| Storage Conditions | Percent Decomposition of A.I.* | Dispersion Stability |
| --- | --- | --- |
| 40° C. | | |
| 1 month | 0 | uniform dispersion without settlement of A.I. |
| 3 months | 0.1 | uniform dispersion without settlement of A.I. |
| 6 months | 0.4 | uniform dispersion without settlement of A.I. |
| 50° C. | | |
| 1 month | 0 | uniform dispersion without settlement of A.I. |
| 3 months | 0.5 | uniform dispersion without settlement of A.I. |
| 6 months | 2.6 | uniform dispersion without settlement of A.I. |

*based on the A.I. content determined at the time of preparation.

EXAMPLE 3

10 g of (±)-α-cyano-3-phenoxybenzyl (±)-2-(4-chlorophenyl)isovalerate was added to 40 g of a 10 wt% aqueous solution of gum arabic, and the mixture was stirred at 70° C. with a T.K. Homomixer at 5000 rpm for a period of 5 minutes. To the mixture was added 50 g of a 0.8 wt% aqueous solution of Rheogic 250H at ambient temperature, and the resultant mixture was lightly stirred for a few minutes to obtain 100 g of a homogeneous oil-in-water insecticidal and acaricidal emulsion containing 10 wt% of (±)-α-cyano-3-phenoxybenzyl (±)-2-(4-chlorophenyl)isovalerate. The particles of the emulsified active ingredient were in the range of from 1 to 80μ in size.

EXAMPLE 4

The procedure of Example 3 was repeated except that the T.K. Homomixer was rotated at 2500 rpm. The product was 100 g of an oil-in-water insecticidal and acaricidal emulsion containing 10 wt% of (±)-α-cyano-3-phenoxybenzyl (±)-2-(4-chlorophenyl)isovalerate. The particles of the emulsified active ingredient were in the range of from 6 to 200μ in size.

EXAMPLE 5

20 g of (±)-α-cyano-3-phenoxybenzyl (±)-2-(4-chlorophenyl)isovalerate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of (±)-α-cyano-3-phenoxybenzyl (±)-2-(4-chlorophenyl)-isovalerate. The particles of the emusified active ingredient were in the range of from 1 to 60μ in size.

EXAMPLE 6

1 g of (±)-α-cyano-3-phenoxybenzyl (±)-2-(4-chlorophenyl)isovalerate was added to 40 g of a 5 wt% aqueous solution of Gohsenol GL-05, and the mixture was stirred at 70° C. with a T.K. Homomixer at 5000 rpm for a period of 5 minutes.

To the mixture was added 59 g of a neutralized 17 wt% aqueous solution of Agrisol FL-100F at ambient temperature, and the resultant mixture was lightly stirred for a few minutes to obtain 100 g of a homogeneous oil-in-water insecticidal and acaricidal emulsion containing 1 wt% of (±)-α-cyano-3-phenoxybenzyl (±)-2-(4-chlorophenyl)isovalerate. The particles of the emulsified active ingredient were in the range of from 1 to 50μ in size.

EXAMPLE 7

40 g of (±)-α-cyano-3-phenoxybenzyl (±)-2-(4-chlorophenyl)isovalerate was added to 50 g of a 20 wt% aqueous solution of Gohsenol GL-05, and the mixture was stirred at 70° C. with a T.K. Homomixer at 5000 rpm for a period of 5 minutes.

To the mixture was added 10 g of a neutralized 50 wt% aqueous solution of Agrisol FL-100F at ambient temperature, and the resultant mixture was lightly stirred for a few minutes to obtain 100 g of a homogeneous oil-in-water insecticidal and acaricidal emulsion containing 40 wt% of (±)-α-cyano-3-phenoxybenzyl (±)-2-(4-chlorophenyl)isovalerate. The particles of the emulsified active ingredient were in the range of from 1 to 40μ in size.

EXAMPLE 8

20 g of α-cyano-3-phenoxybenzyl (±)-2-(4-chlorophenyl)isovalerate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of α-cyano-3-phenoxybenzyl (+)-2-(4-chlorophenyl)isovalerate. The particles of the emulsified active ingredient were in the range of from 1 to 40μ in size.

EXAMPLE 9

40 g of α-cyano-3-phenoxybenzyl (+)-2-(4-chlorophenyl)isovalerate was added to 50 g of 10 wt% aqueous solution of Gohsenol GL-05, and the mixture was stirred at 70° C. with a T.K. Homomixer at 5000 rpm for a period of 5 minutes.

To the mixture was added 10 g of a neutralized 50 wt% aqueous solution of Agrisol FL-100F at ambient temperature, and the resultant mixture was lightly stirred for a few minutes to obtain 100 g of a homogeneous oil-in-water insecticidal and acaricidal emulsion containing 40 wt% of α-cyano-3-phenoxybenzyl (+)-2-(4-chlorophenyl)isovalerate. The particles of the emulsified active ingredient were in the range of from 1 to 30μ in size.

EXAMPLE 10

20 g of a mixture comprising 80% of (−)-α-cyano-3-phenoxybenzyl (+)-2-(4-chlorophenyl)isovalerate and (+)-α-cyano-3-phenoxybenzyl (−)-2-(4-chlorophenyl)isovalerate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of the above insecticidally and acaricidally active ingredients. The particles of the emulsified active ingredients were in the range of from 1 to 40μ in size.

EXAMPLE 11

20 g of (±)-α-cyano-3-(4-bromophenoxy)benzyl (±)-2-(4-chlorophenyl)isovalerate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of (±)-α-cyano-3-(4-bromophenoxy)benzyl (±)-2-(4-chlorophenyl)isovalerate. The particles of the emulsified active ingredient were in the range of from 1 to 50μ in size.

EXAMPLE 12

20 g of (±)-α-cyano-3-phenoxybenzyl (±)-2-(4-tert-butylphenyl)isovelerate was added to 40 g of Gohsenol GL-05, and the mixture was stirred at 70° C. with a T.K. Homomixer at 5000 rpm for a period of 5 minutes.

To the mixture was added 40 g of a neutralized 25 wt% of Agrisol FL-100F at ambient temperature, and the resultant mixture was lightly stirred for a few minutes to obtain 100 g of a homogeneous oil-in-water insecticidal and acaricidal emulsion containing 20 wt% of (±)-α-cyano-3-phenoxybenzyl (±)-2-(4-tert-butylphenyl)isovalerate. The particles of the emulsified active ingredient were in the range of from 1 to 60μ in size.

EXAMPLE 13

20 g of (±)-α-cyano-3-(4-fluorophenoxy)benzyl (±)-2-(4-chlorophenyl)isovalerate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of (±)-α-cyano-3-(4-fluorophenoxy)benzyl (±)-2-(4-chlorophenyl)isovalerate. The particles of the emulsified active ingredient were in the range of from 1 to 50μ in size.

EXAMPLE 14

20 g of (±)-α-cyano-3-(4-bromophenoxy)benzyl (±)-cis,trans-2,2-dimethyl-3-(2,2-dichlorovinyl)cyclopropanecarboxylate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of (±)-α-cyano-3-(4-bromophenoxy)benzyl (±)-cis,trans-2,2-dimethyl-3-(2,2-dichlorovinyl)cyclopropanecarboxylate. The particles of the emulsified active ingredient were in the range of from 1 to 50μ in size.

EXAMPLE 15

20 g of (±)-α-cyano-3-(4-fluorophenoxy)benzyl (±)-cis,trans-2,2-dimethyl-3-(2,2-dichlorovinyl)cyclopropanecarboxylate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of (±)-α-cyano-3-(4-fluorophenoxy)benzyl (±)-cis,trans-2,2-dimethyl-3-(2,2-dichlorovinyl)cyclopropanecarboxylate. The particles of the emulsified active ingredient were in the range of from 1 to 50μ in size.

EXAMPLE 16

20 g of (±)-α-cyano-3-phenoxybenzyl (±)-cis,trans,-crystanthemate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of (±)-α-cyano-3-phenoxybenzyl (±)-cis,trans-chrysanthemate. The particles of the emulsified active ingredient were in the range of from 1 to 50μ in size.

As is clear from Table 3 below which indicates the results of test for dispersion stability, the insecticidal and acaricidal emulsion of this invention was stable in its chemical and physical properties.

TABLE 3

Stability Test for the Insecticidal and Acaricidal Emulsion of Example 16

| Storage Conditions | Percent Decomposition of A.I.* | Dispersion Stability |
| --- | --- | --- |
| 40° C. | | |
| 1 month | 0 | uniform dispersion without settlement of A.I. |
| 3 months | 0.3 | uniform dispersion without settlement of A.I. |
| 6 months | 0.6 | uniform dispersion without settlement of A.I. |
| 50° C. | | |
| 1 month | 0 | uniform dispersion without settlement of A.I. |
| 3 months | 1.0 | uniform dispersion without settlement of A.I. |
| 6 months | 3.5 | uniform dispersion without settlement of A.I. |

*based on the A.I. content determined at the time of preparation

EXAMPLE 17

The procedure of Example 16 was repeated except that the T.K. Homomixer was rotated at 2500 rpm. The product was 100 g of an oil-in-water insecticidal and acaricidal emulsion containing 20 wt% of (±)-α-cyano-3-phenoxybenzyl (±)-cis,trans-chrysanthemate. The particles of the emulsified active ingredient were in the range of from 1 to 130μ in size.

EXAMPLE 18

40 g of α-cyano-3-phenoxybenzyl (+)-cis,trans-chrysanthemate was added to 40 g of a 5 wt% aqueous solution of Gohsenol GL-05, and the mixture was stirred at 70° C. with a T.K. Homomixer at 5000 rpm for a period of 5 minutes.

To the mixture was added 20 g of a neutralized 50 wt% aqueous solution of Agrisol FL-100F at ambient temperature, and the resultant mixture was lightly stirred for a few minutes to obtain 100 g of a homogeneous oil-in-water insecticidal and acaricidal emulsion containing 40 wt% of α-cyano-3-phenoxybenzyl (+)-cis,trans-chrysanthemate. The particles of the emulsified active ingredient were in the range of from 1 to 60μ in size.

EXAMPLE 19

25 g of α-cyano-3-phenoxybenzyl (+)-trans-chrysanthemate was added to 50 g of a 10 wt% aqueous solution of gum arabic, and the mixture was stirred at 70° C. with a T.K. Homomixer at 5000 rpm for a period of 5 minutes. To the mixture was added 25 g of a 2.0 wt% aqueous solution of sodium alginate, and the resultant mixture was lightly stirred for a few minutes to obtain 100 g of a homogeneous oil-in-water insecticidal and acaricidal emulsion containing 25 wt% of α-cyano-3-phenoxybenzyl (+)-trans-chrysanthemate. The particles of the emulsified active ingredient were in the range of from 1 to 50μ in size.

EXAMPLE 20

20 g of (±)-α-cyano-3-phenoxybenzyl (±)-cis,trans-2,2-dimethyl-3-(2,2-dichlorovinyl)cyclopropanecarboxylate was added to 40 g of a 10 wt% aqueous solution of Gohsenol GL-05, and the mixture was stirred at 70° C. with a T.K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal and emulsion containing 20 wt% of (±)-α-cyano-3-phenoxybenzyl (±)-cis,trans-2,2-dimethyl-3-(2,2-dichlorovinyl)cyclopropanecarboxylate. The particles of the emulsified active ingredient were in the range of from 1 to 50μ in size.

As is clear from Table 4 below which indicates the results of test for dispersion stability, the insecticidal and acaricidal emulsion of this invention was stable in its chemical and physical properties.

TABLE 4

Stability Test for the Insecticidal and Acaricidal Emulsion of Example 20

| Storage Conditions | Percent Decomposition of A.I.* | Dispersion Stability |
| --- | --- | --- |
| 40° C. | | |
| 1 month | 0 | uniform dispersion without settlement of A.I. |
| 3 months | 0.7 | uniform dispersion without settlement of A.I. |
| 6 months | 1.2 | uniform dispersion without settlement of A.I. |
| 50° C. | | |
| 1 month | 0 | uniform dispersion without settlement of A.I. |
| 3 months | 1.6 | uniform dispersion without settlement of A.I. |
| 6 months | 3.7 | uniform dispersion without settlement of A.I. |

*based on the A.I. content determined at the time of preparation.

EXAMPLE 21

1 g of (±)-α-cyano-3-phenoxybenzyl (±)-cis,trans-2,2-dimethyl-3-(2,2-dichlorovinyl)cyclopropanecarboxylate was added to 40 g of a 5 wt% aqueous solution of gum arabic, and the mixture was stirred at 70° C. with a T.K. Homomixer at 5000 rpm for a period of 5 minutes. To the mixture was added 59 g of a 2 wt% aqueous solution of sodium carboxymethylcellulose, and the resultant mixture was lightly stirred for a few minutes to obtain 100 g of a homogeneous oil-in-water insecticidal and acaricidal emulsion containing 1 wt% of (±)-α-cyano-3-phenoxybenzyl (±)-cis,trans-2,2-dimethyl-3-(2,2-dichlorovinyl)cyclopropanecarboxylate. The particles of the emulsified active ingredient were in the range of from 1 to 40μ in size.

EXAMPLE 22

30 g of α-cyano-3-phenoxybenzyl (+)-cis,trans-2,2-dimethyl-3-(2,2-dichlorovinyl)cyclopropanecarboxylate was added to 50 g of a 10 wt% aqueous solution of Gohsenol GL-05, and the mixture was stirred at 70° C. with a T.K. Homomixer at 5000 rpm for a period of 5 minutes.

To the mixture was added 20 g of a neutralized 50 wt% aqueous solution of Agrisol FL-100F at ambient temperature, and the resultant mixture was lightly stirred for a few minutes to obtain 100 g of a homogeneous oil-in-water insecticidal and acaricidal emulsion containing 30 wt% of α-cyano-3-phenoxybenzyl (+)-cis,trans-2,2-dimethyl-3-(2,2-dichlorovinyl)cyclopropanecarboxylate. The particles of the emulsified active ingredient were in the range of from 1 to 50μ in size.

EXAMPLE 23

5 g of α-cyano-3-phenoxybenzyl (+)-trans-2,2-dimethyl-3-(2,2-dichlorovinyl)cyclopropanecarboxylate was added to 45 g of a 5 wt% aqueous solution of gum arabic, and the mixture was stirred at 70° C. with a T.K. Homomixer at 2500 rpm for a period of 5 minutes. To the mixture was added 50 g of a 0.8 wt.% aqueous solution of Rheogic 250H at ambient temperature, and the resultant mixture was stirred lightly for a few minutes to obtain 100 g of a homogeneous oil-in-water insecticidal and acaricidal emulsion containing 5 wt% of α-cyano-3-phenoxybenzyl (+)-trans-2,2-dimethyl-3-(2,2-dichlorovinyl)cyclopropanecarboxylate. The particles of the emulsified active ingredient were in the range of from 1 to 140μ in size.

EXAMPLE 24

20 g of (±)-α-cyano-3-phenoxybenzyl 2,2,3,3-tetramethylcyclopropanecarboxylate was added to 40 g of a 10 wt% aqueous solution of Gohsenol GL-05, and the mixture was stirred at 70° C. with a T. K. Homomixer at 5000 rpm for a period of 5 minutes.

To the mixture was added 40 g of a neutralized 25 wt% aqueous solution of Agrisol FL-100F at ambient temperature, and the resultant mixture was lightly stirred for a few minutes to obtain 100 g of a homogeneous oil-in-water insecticidal and acaricidal emulsion containing 20 wt% of (±)-α-cyano-3-phenoxybenzyl-2,2,3,3-tetramethylcyclopropanecarboxylate. The particles of the emulsified active ingredient were in the range of from 1 to 40μ in size.

The following experiment was conducted to demonstrate the effectiveness of gum arabic and polyvinyl alcohol as a dispersing agent compared with other water soluble polymers.

Experiment 1

180 g of a 2 wt% aqueous solution of each of the following substances was prepared: alubumin, cellulose sulfate derivative, sodium alginate, carrageenan, polyvinyl pyrrolidone, carboxymethylcellulose, sodium lignin sulfonate, gelatin, gum arabic and Gohsenol GL-05. To each of the aqueous solutions was added 20 g of each of the nine hydrophobic insecticidally and acaricidally active liquid ingredients of the formula (I) in a racemic form indicated in Table 5 below. A T. K. Homomixer was used to disperse the active ingredients at 70° C. until their emulsified particles were from 1 to 100μ in size, and each of the resulting emulsions was put in a sealable glass container which was stored in a constant temperature dryer at 60° C. for one day, and observed for its dispersion stability. The results of the observation are set forth in Table 5 below.

TABLE 5

| Insecticidal and Acaricidal Compound | Evaluation of Dispersion Stability — Water Soluble Polymer | | | | | | | | | |
|---|---|---|---|---|---|---|---|---|---|---|
| | Alubumin | Cellulose Sulfate Derivative | Sodium Alginate | Carrageenan | Polyvinyl Pyrrolidone | Carboxymethylcellulose | Sodium Lignin Sulfonate | Gelatin | Gum Arabic | Gohsenol GL-05 |
| (1) | X | X | X | Δ | X | X | Δ | X | O | O |
| (2) | X | X | X | Δ | X | X | Δ | X | O | O |
| (3) | X | X | X | Δ | X | X | Δ | X | O | O |
| (4) | X | X | X | Δ | X | X | Δ | X | O | O |
| (5) | X | X | X | Δ | X | X | Δ | X | O | O |
| (6) | X | X | X | Δ | X | X | Δ | X | O | O |
| (7) | X | X | X | Δ | X | X | Δ | X | O | O |
| (8) | X | X | X | Δ | X | X | Δ | X | O | O |
| (9) | X | X | X | Δ | X | X | Δ | X | O | O |

Criteria for evaluation of dispersion stability
O . . no trace of agglomeration of particles of active ingredient
Δ . . particles of active ingredient agglomerated, but no separation occurred between oil phase and aqueous phase
X . . particles of active ingredient agglomerated until oil phase separated from aqueous phase In Table 5 above, insecticidal and acaricidal compounds (1) to (9) have the following formulae:

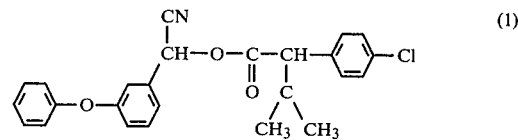 (1)

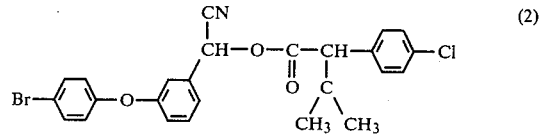 (2)

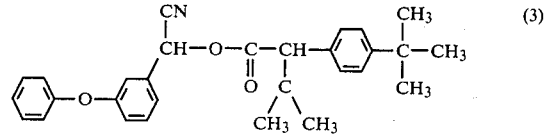 (3)

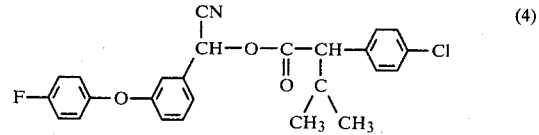 (4)

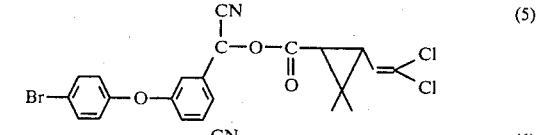 (5)

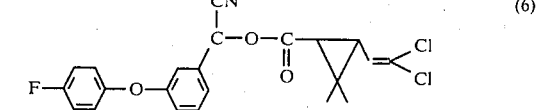 (6)

Experiment 4

To evaluate the irritating effect of the oil-in-water insecticidal and acaricidal emulsion of this invention on mucous membranes, the irritating effect of the emulsion on the eyes of a rabbit was examined in accordance with the Environmental Protection Agency Guideline [*Federal Register*, 43, 37359–37360 (1978)].

In this test the five oil-in-water insecticidal and acaricidal emulsions containing 20 wt% of active ingredient prepared in Examples 5, 8, 10, 20 and 24 (hereunder referred to as Emulsions, 5, 8, 10, 20 and 24, respectively) were compared with an equal number of control formulation (emulsifiable concentrate containing 20 wt% of an active ingredient the same as employed in the above five oil-in-water insecticidal and acaricidal emulsions, and these controls are hereunder referred to as Control Formulations C-5, C-8, C-10, C-20 and C-24, respectively). The results obtained are shown in Table 8 below, in which the maximum total score of the strength of irritation reaction and the strength of irritation was obtained in accordance with the standard shown in Table 9 below.

TABLE 8

| Active ingredient | Emulsion/ Control Formulation | Organism | | 1 hr. | 24 hrs. | 48 hrs. | 72 hrs. | 96 hrs. | 7 days | Maximum total point |
|---|---|---|---|---|---|---|---|---|---|---|
| (±)-α-Cyano-3-phenoxybenzyl (±)-2-(4-chlorophenyl)-isovalerate | 5 | Cornea | Opacity-degree of density | 0 | 0 | 0 | 0 | 0 | 0 | |
| | | | Area of cornea involved | 0 | 0 | 0 | 0 | 0 | 0 | |
| | | Iris | | 0 | 0 | 0 | 0 | 0 | 0 | |
| | | Conjunctivae | Redness | 1 | 1–2 | 0 | 0 | 0 | 0 | |
| | | | Chemosis | 0 | 0 | 0 | 0 | 0 | 0 | |
| | | | Discharge | 0 | 0 | 0 | 0 | 0 | 0 | 2.7/110 |
| | C-5 | Cornea | Opacity-degree of density | 0 | 1 | 1 | 1 | 1 | 1 | |
| | | | Area of cornea involved | 0 | 4 | 4 | 4 | 2–4 | 2–4 | |
| | | Iris | | 0 | 0 | 0 | 0 | 0 | 0 | |
| | | Conjunctivae | Redness | 1 | 1 | 1 | 1 | 1 | 0 | |
| | | | Chemosis | 2 | 1 | 0 | 0 | 0 | 0 | |
| | | | Discharge | 0 | 1 | 1 | 0 | 0 | 0 | 26.0/110 |
| α-Cyano-3-phenoxybenzyl (+)-2-(4-chlorophenyl)-isovalerate | 8 | Cornea | Opacity-degree of density | 0 | 0 | 0 | 0 | 0 | 0 | |
| | | | Area of cornea involved | 0 | 0 | 0 | 0 | 0 | 0 | |
| | | Iris | | 0 | 0 | 0 | 0 | 0 | 0 | |
| | | Conjunctivae | Redness | 1 | 1–2 | 0–1 | 0 | 0 | 0 | |
| | | | Chemosis | 0–1 | 0 | 0 | 0 | 0 | 0 | |
| | | | Discharge | 0 | 1 | 0 | 0 | 0 | 0 | 5.3/110 |
| | C-8 | Cornea | Opacity-degree of density | 0 | 1 | 1 | 1 | 1 | 1 | |
| | | | Area of cornea involved | 0 | 4 | 4 | 4 | 2–4 | 2–3 | |
| | | Iris | | 0 | 1 | 1 | 1 | 1 | 0 | |
| | | Conjunctivae | Redness | 1 | 2 | 2 | 2 | 1–2 | 1 | |
| | | | Chemosis | 2 | 2 | 0 | 0 | 0 | 0 | |
| | | | Discharge | 0 | 2 | 2–3 | 1–2 | 0 | 0 | 35.7/110 |
| Mixture of (−)-α-cyano-3-phenoxybenzyl (+)-2-(4-chlorophenyl)-isovalerate and (+)-α-cyano-3-phenoxybenzyl (−)-2-(4-chlorophenyl)-isovalerate | 10 | Cornea | Opacity-degree of density | 0 | 0 | 0 | 0 | 0 | 0 | |
| | | | Area of cornea involved | 0 | 0 | 0 | 0 | 0 | 0 | |
| | | Iris | | 0 | 0 | 0 | 0 | 0 | 0 | |
| | | Conjunctivae | Redness | 1 | 2 | 0–1 | 0 | 0 | 0 | |
| | | | Chemosis | 0 | 0 | 0 | 0 | 0 | 0 | |
| | | | Discharge | 0 | 1–2 | 0 | 0 | 0 | 0 | 8.4/110 |
| | C-10 | Cornea | Opacity-degree of density | 0 | 1 | 1 | 1 | 1 | 1 | |
| | | | Area of cornea involved | 0 | 4 | 4 | 4 | 2–4 | 2–4 | |
| | | Iris | | 0 | 1 | 0–1 | 0–1 | 0–1 | 0 | |
| | | Conjunctivae | Redness | 1 | 2 | 1–2 | 1–2 | 1–2 | 1 | |
| | | | Chemosis | 2 | 1–2 | 0 | 0 | 0 | 0 | |
| | | | Discharge | 0 | 1 | 1–2 | 0–1 | 0 | 0 | 34.3/110 |
| (±)-α-Cyano-3-phenoxybenzyl (±)-cis, trans-2,2-dimethyl-3-(2,2-dichlorovinyl)cyclopropanecarboxylate | 20 | Cornea | Opacity-degree of density | 0 | 0 | 0 | 0 | 0 | 0 | |
| | | | Area of cornea involved | 0 | 0 | 0 | 0 | 0 | 0 | |
| | | Iris | | 0 | 0–1 | 0 | 0 | 0 | 0 | |
| | | Conjunctivae | Redness | 1 | 2 | 0–1 | 0 | 0 | 0 | |
| | | | Chemosis | 0 | 0 | 0 | 0 | 0 | 0 | |
| | | | Discharge | 0 | 0 | 0 | 0 | 0 | 0 | 5.7/110 |
| | C-20 | Cornea | Opacity-degree of density | 0 | 1 | 1 | 1 | 1 | 1 | |
| | | | Area of cornea involved | 0 | 4 | 4 | 2–4 | 2–4 | 2–4 | |
| | | Iris | | 0 | 1 | 1 | 0–1 | 0–1 | 0–1 | |

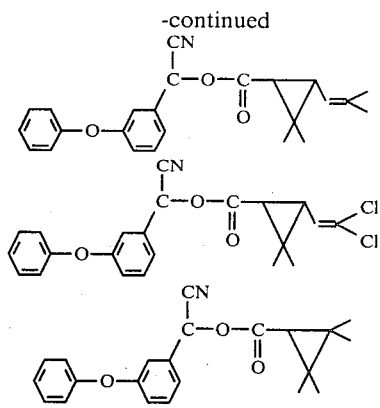

Table 5 clearly indicates the effectiveness of gum arabic and polyvinyl alcohol as a dispersing agent.

The following experiment was conducted to demonstrate the effectiveness of the oil-in-water insecticidal and acaricidal emulsion prepared by this invention.

Experiment 2

The eleven oil-in-water insecticidal and acaricidal emulsions containing 20 wt% of active ingredient prepared in Examples 5, 8, 10, 11, 12, 13, 14, 15, 16, 20 and 24 (hereunder referred to as Emulsions 5, 8, 10, 11, 12, 13, 14, 15, 16, 20 and 24, respectively) were compared with an equal number of control formulations (emulsifiable concentrate containing 20 wt% of an active ingredient the same as employed in the above eleven oil-in-water insecticidal and acaricidal emulsions, and these controls are hereunder referred to as Control Formulations C-5, C-8, C-10, C-11, C-12, C-13, C-14, C-15, C-16, C-20 and C-24, respectively) in the following manner. A solution containing the oil-in-water insecticidal and acaricidal emulsion or the control formulation in each of the concentrations indicated in Table 6 below was applied to young Chinese cabbage leaves on a turntable at a rate of 30 ml/2 pots. After drying in air, the treated leaves were put in a plastic cup together with a group of ten (3–4 instar) tobacco cutworm (*Spodoptera litura*) larvae, and the number of mortalities at the end of the second day was counted. The results of the mortality test are shown in Table 6 below.

TABLE 6

| Emulsion/Control Formulation | Percent Mortality of Tobacco Cutworm (*Spodoptera litura*) | |
|---|---|---|
| | 50 ppm | 100 ppm |
| 5 | 100 | 100 |
| C-5 | 100 | 100 |
| 8 | 100 | 100 |
| C-8 | 100 | 100 |
| 10 | 100 | 100 |
| C-10 | 100 | 100 |
| 11 | 100 | 100 |
| C-11 | 100 | 100 |
| 12 | 100 | 100 |
| C-12 | 100 | 100 |
| 13 | 100 | 100 |
| C-13 | 100 | 100 |
| 14 | 100 | 100 |
| C-14 | 100 | 100 |
| 15 | 100 | 100 |
| C-15 | 100 | 100 |
| 16 | 100 | 100 |
| C-16 | 100 | 100 |
| 20 | 100 | 100 |
| C-20 | 100 | 100 |
| 24 | 100 | 100 |
| C-24 | 100 | 100 |

As is clear from the above table, all samples of the oil-in-water insecticidal and acaricidal emulsion of this invention proved to have an excellent effect equivalent to the control formulation at either dilution ratio, but the emulsion of this invention is easier to use.

Experiment 3

Twenty adult female citrus red mites (*Panonychus citri*) were released on the back surface of each leaf of a citrus, the front surface of which had been brought into intimate contact with water-containing absorbent cotton. Three m of each solution of Emulsions 5, 8, 10, 11, 12, 13, 14, 15, 16, 20 and 24 and Control Formulations C-5, C-8, C-10, C-11, C-12, C-13, C-14, C-15, C-16, C-20 and C-24 prepared by diluting the emulsion or control formulation with water to a concentration of 500 ppm, was applied to the leaf. Twenty-four hours after the application, the number of alive mites was counted. This test was repeated three times to thereby obtain an average percent mortality of citrus red mite (*Panonychus citri*). The results obtained are shown in Table 7 below.

TABLE 7

| Emulsion/Control Formulation | Percent Mortality of Citrus Red Mite (*Panonychus citri*) at 500 ppm |
|---|---|
| 5 | 100 |
| C-5 | 100 |
| 8 | 100 |
| C-8 | 100 |
| 10 | 100 |
| C-10 | 100 |
| 11 | 100 |
| C-11 | 100 |
| 12 | 100 |
| C-12 | 100 |
| 13 | 100 |
| C-13 | 100 |
| 14 | 100 |
| C-14 | 100 |
| 15 | 100 |
| C-15 | 100 |
| 16 | 100 |
| C-16 | 100 |
| 20 | 100 |
| C-20 | 100 |
| 24 | 100 |
| C-24 | 100 |

It is also clear from the above table that all samples of the oil-in-water insecticidal and acaricidal emulsion of this invention proved an excellent effect equivalent to the control formulation, but the emulsion of this invention is easier to use.

Another experiment was conducted to demonstrate that, compared with the conventional insecticidal and acaricidal formulation, the oil-in-water insecticidal and acaricidal emulsion of this invention is less irritating to the eyes of a rabbit as one example of humans, cattle or other domestic animals or poultry.

TABLE 8-continued

| Active ingredient | Emulsion/ Control Formulation | Organism | | Irritation Strength | | | | | | |
|---|---|---|---|---|---|---|---|---|---|---|
| | | | | 1 hr. | 24 hrs. | 48 hrs. | 72 hrs. | 96 hrs. | 7 days | Maximum total point |
| | | Conjunctivae | Redness | 1 | 2 | 2 | 1-2 | 1-2 | 1 | |
| | | | Chemosis | 2 | 0-1 | 0 | 0 | 0 | 0 | |
| | | | Discharge | 0 | 1-2 | 1-2 | 1-2 | 1 | 0 | 32.3/110 |
| | | Cornea | Opacity-degree of density | 0 | 0 | 0 | 0 | 0 | 0 | |
| | | | Area of cornea involved | 0 | 0 | 0 | 0 | 0 | 0 | |
| | 24 | Iris | | 0 | 0 | 0 | 0 | 0 | 0 | |
| (±)-α-Cyano-3-phenoxybenzyl-2,2,3,3-tetramethyl-cyclopropane-carboxylate | | Conjunctivae | Redness | 1 | 1-2 | 0 | 0 | 0 | 0 | |
| | | | Chemosis | 0 | 0 | 0 | 0 | 0 | 0 | |
| | | | Discharge | 0 | 0-1 | 0 | 0 | 0 | 0 | 3.3/110 |
| | | Cornea | Opacity-degree of density | 0 | 1 | 1 | 1 | 1 | 1 | |
| | | | Area of cornea involved | 0 | 4 | 4 | 4 | 2-4 | 2-3 | |
| | C-24 | Iris | | 0 | 1 | 0-1 | 0 | 0 | 0 | |
| | | Conjunctivae | Redness | 1-2 | 2 | 2 | 2 | 1-2 | 1-2 | |
| | | | Chemosis | 2 | 1-2 | 0 | 0 | 0 | 0 | |
| | | | Discharge | 0 | 1-2 | 1-2 | 0-1 | 0 | 0 | 34.3/110 |

TABLE 9

Scale for Scoring Ocular Lesions

1. Cornea
(A) Opacity - degree of density (area taken for reading)
No opacity  0
Scattered or diffuse area - details of iris clearly visible  1
Easily discernible translucent areas, details of iris slightly obscured  2
Opalescent areas, no details of iris visible, size of pupil barely discernible  3
Opaque, iris invisible  4
(B) Area of cornea involved
One quarter (or less) but not zero  1
Greater than one quarter - less than one-half  2
Greater than one-half less than three quarters  3
Greater than three quarters up to whole area  4
Score equals A × B × 5 Total maximum = 80
2. Iris
(A) Values
Normal  0
Folds above normal, congestion, swelling, circumcorneal injection
(any one or all of these or combination of any thereof), iris still reacting to light (sluggish reaction is positive)  1
No reaction to light, hemorrhage; gross destruction
(any one or all of these)  2
Score A × 5 Total possible maximum = 10
3. Conjunctivae
(A) Redness (refers to palpebral conjunctivae only)
Vessels normal  0
Vessels definitely injected above normal  1
More diffuse, deeper crimson red, individual vessels not easily discernible  2
Diffuse beefy red  3
(B) Chemosis
No swelling  0
Any swelling above normal (includes nictitation membrane)  1
Obvious swelling with partial eversion of the lids  2
Swelling with lids about half closed  3
Swelling with lids about half closed to completely closed  4
(C) Discharge
No discharge  0
Any amount different from normal (does not include small amount observed in inner canthus of normal animals)  1
Discharge with moistening of the lids and hairs just adjacent to the lids  2
Discharge with moistening of the lids and considerable area around the eye  3
Score (A + B + C) × 2 Total maximum = 20

The maximum total score is the sum of all scores obtained for the cornea, iris and conjunctivae.

It was confirmed from Table 8 above that the degree of irritation of the oil-in-water insecticidal and acaricidal emulsion of this invention is weaker than that of the control formulation containing the same active ingredient as that in the emulsion of this invention.

Still another experiment was conducted to demonstrate that, compared with the conventional insecticidal and acaricidal formulations, the oil-in-water insecticidal and acaricidal emulsion of this invention is less toxic to humans, cattle or other domestic animals or poultry, and therefore is considered to be less hazardous in handling.

EXPERIMENT 5

To evaluate the degree of toxicity of the oil-in-water insecticidal and acaricidal emulsion of this invention, the acute oral toxicity of the emulsion in mice was examined. The test samples and control formulations were the same as used in Experiment 4 above.

The test was conducted by orally administering a diluted solution of each sample (diluted with distilled water) to groups of dd-strain mice (one group = 10 male mice plus 10 female mice) at a dose of 20 ml/kg per mouse and 2 weeks after the administration, observing the number of dead mice. The results obtained are shown in Table 10 below, in which the $LD_{50}$ value was obtained in accordance with the method proposed by Litchfield and Wilcoxon (see *J. Pharmcol. Exptl. Therp.*, 96, 99 (1949)).

TABLE 10

| Active Ingredient | Emulsion/ Control Formulation | $LD_{50}$ (mg/kg) | |
|---|---|---|---|
| | | Male | Female |
| (±)-α-Cyano-3-phenoxybenzyl (±)-2-(4-chlorophenyl)-isovalerate | 5 | 1530 | 1990 |
| | C-5 | 330 | 300 |
| α-Cyano-3-phenoxybenzyl (+)-2-(4-chlorophenyl)-isovalerate | 8 | 983 | 786 |
| | C-8 | 164 | 143 |
| Mixture of (−)-α-cyano-3-phenoxybenzyl (+)-2-(4-chlorophenyl)isovalerate and (+)-α-cyano-3-phenoxybenzyl (−)-2-(4-chlorophenyl)isovalerate | 10 | 803 | 766 |
| | C-10 | 191 | 192 |
| (±)-α-Cyano-3-phenoxybenzyl (±)-cis, trans-2,2-dimethyl-3-(2,2-dichlorovinyl)cyclo-propanecarboxylate | 20 | 475 | 531 |
| | C-20 | 147 | 216 |
| (±)-α-Cyano-3-phenoxybenzyl | 24 | 230 | 217 |

TABLE 10-continued

| Active Ingredient | Emulsion/Control Formulation | LD$_{50}$ (mg/kg) Male | Female |
|---|---|---|---|
| 2,2,3,3-tetramethylcyclopropane-carboxylate | C-24 | 103 | 97.4 |

As is clear from Table 10 above, the acute oral toxicity in mice of the oil-in-water insecticidal and acaricidal emulsion of this invention was less than that of the control formulation containing the same active ingredient as that in the emulsion of this invention.

While the invention has been described in detail and with reference to specific embodiments thereof, it will be apparent to one skilled in the art that various changes and modifications can be made therein without departing from the spirit and scope thereof.

What is claimed is:

1. An oil-in-water insecticidal and acaricidal emulsion comprising as a hydrophobic insecticidally and acaricidally active liquid ingredient 1 to 50% by weight of at least one ester of the formula (I):

$$X-\underset{}{\bigcirc}-O-\underset{}{\bigcirc}-\underset{\underset{CN}{|}}{CH}-O-\underset{\underset{O}{\|}}{C}-Y \quad (I)$$

where X is a hydrogen atom, a chlorine atom, a bromine atom or a fluorine atom; and Y is a group of the formula:

$$-CH-\underset{\underset{H_3C}{}\underset{}{\diagup}\underset{CH_3}{\diagdown}}{\overset{}{C}}\underset{R_2}{\overset{R_1}{\diagup}} \quad \text{or} \quad -\underset{\underset{R_4}{|}}{CH}-\underset{}{\bigcirc}-R_3$$

where R$_1$ is a methyl group or a group of the formula:

$$\underset{H}{\diagdown}C=C\underset{R_5}{\diagup}\underset{R_5}{\diagdown}$$

where R$_5$ is a chlorine atom, a bromine atom, a fluorine atom or a methyl group; R$_2$ is a hydrogen atom or a methyl group; R$_3$ is a chlorine atom, a bromine atom, a fluorine atom or a tert-butyl group; and R$_4$ is an isopropyl group or a cyclopropyl group, 2 to 10% by weight of polyvinyl alcohol or gum arabic and 0.1 to 20% by weight of a thickener with the balance being water.

2. The oil-in-water insecticidal and acaricidal emulsion of claim 1, which contains 1 to 40% by weight of a hydrophobic insecticidally and acaricidally active liquid ingredient comprising an ester of the formula (I) and 0.4 to 10% by weight of a thickener.

3. The oil-in-water insecticidal and acaricidal emulsion of claim 1, wherein the ester of the formula (I) is (±)-α-cyano-3-phenoxybenzyl (±)-2-(4-chlorophenyl)isovalerate.

4. The oil-in-water insecticidal and acaricidal emulsion of claim 1, wherein the ester of the formula (I) is α-cyano-3-phenoxybenzyl (+)-2-(4-chlorophenyl)isovalerate.

5. The oil-in-water insecticidal and acaricidal emulsion of claim 1, wherein the ester of the formula (I) is a mixture comprising more than 60% of (−)-α-cyano-3-phenoxybenzyl (+)-2-(4-chlorophenyl)isovalerate and (+)-α-cyano-3-phenoxybenzyl (−)-2-(4-chlorophenyl)isovalerate.

6. The oil-in-water insecticidal and acaricidal emulsion of claim 1, wherein the ester of the formula (I) is α-cyano-3-(4-bromophenoxy)benzyl 2,2-dimethyl-3-(2,2-dichlorovinyl)-cyclopropanecarboxylate.

7. The oil-in-water insecticidal and acaricidal emulsion of claim 1, wherein the ester of the formula (I) is α-cyano-3-phenoxybenzyl chrysanthemate.

8. The oil-in-water insecticidal and acaricidal emulsion of claim 1, wherein the ester of the formula (I) is (±)-α-cyano-3-phenoxybenzyl (±)-cis,trans-2,2-dimethyl-3-(2,2-dichlorovinyl)cyclopropanecarboxylate.

9. The oil-in-water insecticidal and acaricidal emulsion of claim 1, wherein the ester of the formula (I) is α-cyano-3-phenoxybenzyl (+)-cis,trans-2,2-dimethyl-3-(2,2-dichlorovinyl)cyclopropanecarboxylate.

10. The oil-in-water insecticidal and acaricidal emulsion of claim 1, wherein the ester of the formula (I) is α-cyano-3-phenoxybenzyl 2,2,3,3-tetramethylcyclopropanecarboxylate.

11. A method for the preparation of the oil-in-water insecticidal and acaricidal emulsion of claim 1, which comprises adding a hydrophobic insecticidally and acaricidally active liquid ingredient of the formula (I):

$$X-\underset{}{\bigcirc}-O-\underset{}{\bigcirc}-\underset{\underset{CN}{|}}{CH}-O-\underset{\underset{O}{\|}}{C}-Y \quad (I)$$

where X is a hydrogen atom, a chlorine atom, a bromine atom or a fluorine atom; and Y is a group of the formula:

$$-CH-\underset{\underset{H_3C}{}\underset{}{\diagup}\underset{CH_3}{\diagdown}}{\overset{}{C}}\underset{R_2}{\overset{R_1}{\diagup}} \quad \text{or} \quad -\underset{\underset{R_4}{|}}{CH}-\underset{}{\bigcirc}-R_3$$

where R$_1$ is a methyl group or a group of the formula:

$$\underset{H}{\diagdown}C=C\underset{R_5}{\diagup}\underset{R_5}{\diagdown}$$

where R$_5$ is a chlorine atom, a bromine atom, a fluorine atom or a methyl group; R$_2$ is a hydrogen atom or a methyl group; R$_3$ is a chlorine atom, a bromine atom, a fluorine atom or a tert-butyl group; and R$_4$ is an isopropyl group or a cyclopropyl group, to an aqueous solution of polyvinyl alcohol or gum arabic, stirring the mixture while heating at 60° to 70° C. to form emulsified particles of the active ingredient, and then adding thereto a thickener to stabilize the emulsion.

12. A method for killing insects and acarids which comprises contacting said insects and acarids with an insecticidally and acaricidally effective amount of the oil-in-water insecticidal and acaricidal emulsion of claim 1.

* * * * *